United States Patent [19]

Weiss et al.

[11] Patent Number: 5,574,197
[45] Date of Patent: Nov. 12, 1996

[54] METHOD OF MAKING A STABLE NON-PYROPHORIC LITHIUM DIORGANOAMIDE SOLUTION

[75] Inventors: Wilfried Weiss, Oberursel; Ulrich Wietelmann, Friedrichsdorf; Uwe Lischka; Ute Emmel, both of Frankfurt am Main, all of Germany

[73] Assignee: Metallgesellschaft Aktiengesellschaft, Frankfurt am Main, Germany

[21] Appl. No.: 311,525

[22] Filed: Sep. 23, 1994

[30] Foreign Application Priority Data

Sep. 27, 1993 [DE] Germany ............ 43 32 652.8

[51] Int. Cl.⁶ .................. C07C 7/20; C01D 15/00
[52] U.S. Cl. .................. 585/4; 564/2; 564/463; 423/179.5
[58] Field of Search ............ 585/4; 564/2, 463; 423/179.5

[56] References Cited

U.S. PATENT DOCUMENTS

| | | | |
|---|---|---|---|
| 4,595,779 | 6/1986 | Morrison et al. | 564/2 |
| 5,068,368 | 11/1991 | Smith et al. | 568/780 |
| 5,391,824 | 2/1995 | Smith | 564/2 |

FOREIGN PATENT DOCUMENTS

| | | |
|---|---|---|
| 3905857 | 7/1989 | Germany. |
| 8603744 | 3/1986 | WIPO. |

OTHER PUBLICATIONS

Liebigs Annalen Der Chemie, vol. 1980–No. 10, pp. 1471–1473, Reetz, et al., Oct. 1980.

*Primary Examiner*—Anthony McFarlane
*Assistant Examiner*—E. D. Irzinski
*Attorney, Agent, or Firm*—Michael J. Striker

[57] ABSTRACT

The method of making the stable non-pyrophoric solution containing a lithium diorganoamide of the formula, LiNR'R" wherein R' and R" each have from 2 to 6 carbon atoms, in an inert liquid hydrocarbon solvent includes mixing a secondary amine including the R' and R" groups and an alcohol having 3 to 6 carbon atoms with a lithium granulate or powder in the hydrocarbon solvent and reacting the secondary amine, the alcohol and the lithium with addition of an electron acceptor compound, advantageously styrene or isobutene, to form the stable non-pyrophoric solution containing the lithium diorganoamide and a lithium alkoxide having 3 to 6 carbon atoms.

7 Claims, 1 Drawing Sheet

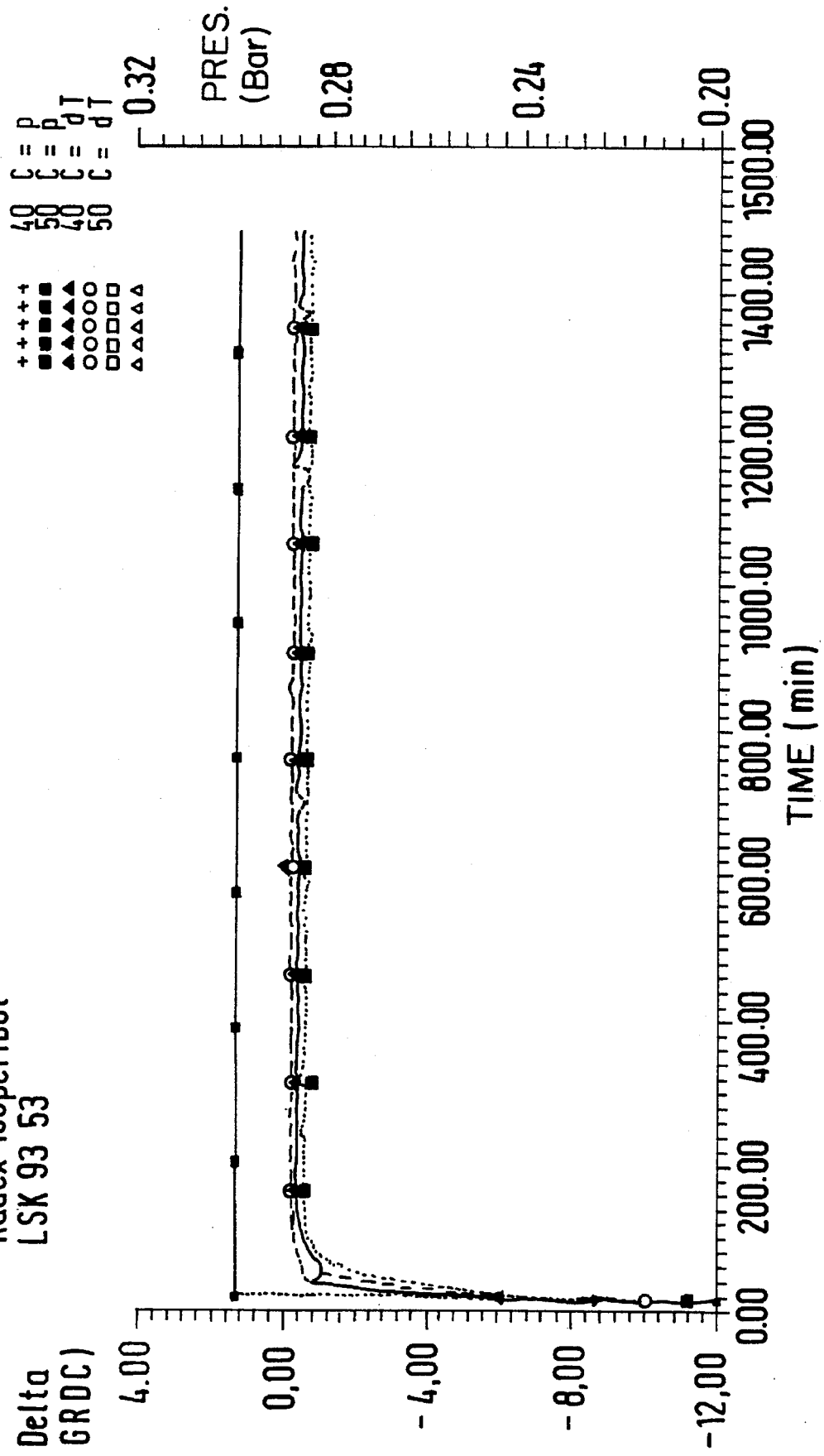

METHOD OF MAKING A STABLE NON-PYROPHORIC LITHIUM DIORGANOAMIDE SOLUTION

BACKGROUND OF THE INVENTION

The present invention relates to stable non-pyrophoric solutions of lithium diorganoamides and processes for preparing them.

Due to their high Bronsted basicity and their low nucleophilicity, lithium diorganoamides, particularly lithium diisopropylamide (LDA), are used on a large scale for the synthetic preparation of pharmaceutical products and as specialty chemicals. Lithium diorganoamides have only a low solubility in hydrocarbon solvents and usually in such solvents an irreversible precipitation of oligomeric or polymeric crystallites of lithium diorganoamide occurs. For this reason, solutions of lithium diorganoamides in hydrocarbons are not commercially available. Whereas lithium diorganoamides are very soluble in ethers, such solutions are not conventional, because they decompose very quickly at room temperature. For this reason numerous users prepare lithium diorganoamides in the required amounts immediately before they are used. Their preparation is usually carried out by reaction of n-butyl lithium with diisopropylamine in cold tetrahydrofuran. But that preparation involves safety risks for those users who are not skilled in the handling the highly reactive organolithium compounds. Besides, the synthesis of lithium diisopropylamide by the reaction of lithium metal with diisopropylamine in diethyl ether in the presence of styrene or isobutene as electron acceptors is known from M. T. Reetz and W. F. Maier, Liebigs' Annalen der Chemie, 10, pp. 1471 to 1473 (1980).

The Patent document WO-86/03 744 discloses stable non-pyrophoric solutions of lithium diisopropylamide in a hydrocarbon solvent. These solutions contain a limited amount of tetrahydrofuran. The main disadvantage of lithium diisopropylamide in ethereal solutions or in hydrocarbon solutions which contain tetrahydrofuran in a limited amount of <1.0 mole per mole of LDA is their limited stability. Solutions of LDA with an equimolar content of THF at maximum exhibit a significant loss of activity (25 to 50%) when stored at 30° to 40° C. for 30 days. On the other hand, only a small loss of activity has been observed during that time at temperatures from 0° to 10° C. But at storage temperatures <0° C. crystallization occurs in more than 2.0-molar solutions of LDA and THF.

German Patent Application DE-A-39 05 857 discloses bimetal diorganoamide compositions, particularly Li-Mg-bis-diorganoamides, in liquid hydrocarbon solvents. These compositions are solutions which have a higher thermal stability and better stability against precipitation than the pure lithium diorganoamide solutions.

Due to the presence of a second metal and/or a metal salt, purifying operations are required after one of these compositions has been used for a synthesis. Besides, the stability of these compositions over a comparatively long time should be improved because of the necessary presence of Lewis bases, such as THF, methyl THF, dimethyl ether, diethyl ether, dibutyl ether or tertiary amines, such as trimethylamine, triethylamine or tetramethylethylenediamine.

SUMMARY OF THE INVENTION

It is an object of the present invention to provide a process for making a stable non-pyrophoric solution of a lithium diorganoamide without the use of the known stabilizing additives.

According to the invention the method is designed to form a stable non-pyrophoric solution of a lithium alkoxide having 3 to 6 carbon atoms and a lithium diorganoamide having a formula, Li NR'R", in an inert liquid hydrocarbon, wherein R' and R" are independently selected from the group consisting of alkyl groups having 2 to 6 carbon atoms.

In preferred embodiments of the invention the R' or R" is an ethyl group, an isopropyl group or a cyclohexyl group. The isopropyl group is preferred for use with the lithium diisopropylamide because of the reactivity of the latter.

The lithium alkoxide contained in the solution is preferably a tertiary alkoxide. If a lithium alkoxide is used, foreign atoms do not enter the solution and the solution can be more easily prepared. Particularly the alkoxide derived from tertiary alcohols, and especially the alkoxide of tert-pentanol, tert-butanol and isopropanol, surprisingly exhibit a very strong stabilizing activity. In a preferred embodiment of the invention the mole ratio of the lithium diorganoamide to alkoxide in the solution is from 100/2 to 100/10. The inert liquid hydrocarbons used desirably include aliphatic, cycloaliphatic, aromatic or alkylaromatic hydrocarbons having 5 to 10 carbon atoms or mixtures of these solvents. Hexane and cyclohexane are particularly preferred as solvents.

The concentration of the lithium diorganoamide in solution is in the range from 0.1 to 2.0 moles per kilogram, preferably from 0.5 to 1.0 mole per kilogram. These solutions have a sufficiently high crystallization stability and a sufficiently high concentration in conjunction with a viscosity which permits them to be handled easily.

A solution of a lithium diorganoamide which is stable in storage for a long time can surprisingly be prepared by adding a secondary amine and an alcohol having 3 to 6 carbon atoms to lithium granulate or lithium powder in an inert liquid hydrocarbon solution and adding an electron acceptor, such as styrene or isobutene, to start a reaction.

In spite of its alcohol content, the solution prepared in accordance with the invention is a very good synthesis composition for use in metallizing or deprotonating reactions.

The subject matter of the invention is now explained more in further detail by the following examples.

EXAMPLES

Example 1

In an inertized 2-liter three-neck round-bottom flask provided with a gas inlet, thermometer and dropping funnel, 695 millimoles DIPA and 0.2 grams lithium hydride in 600 milliliters hexane were added to 650 millimoles lithium powder. The reaction mixture was stirred for about 30 minutes. To the suspension 30 millimoles t-butanol as a one to one mixture with hexane was added and heated up to the boiling point. At the boiling point 310 millimoles styrene were added in a one to one mixture with hexane.

The reaction mixture was filtered with the aid of a G 4-frit after cooling down. 490 grams of a clear yellow filtrate were obtained, which had an active lithium content of 1.09 millimoles per gram active base content of 1.08 millimoles per gram determined by titration with benzoic acid and 4-phenyl-azodiphenylamine as color indicator. This corresponds to a yield of 85.3% LDA.

While the invention has been illustrated and described as embodied method of making a non-pyrophoric solution of a lithium diorganoamide, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. A method of preparing a stable non-pyrophoric solution of a lithium diorganoamide of the formula, LiNR'R" wherein R' and R" are each independently selected from the group consisting of alkyl groups having 2 to 6 carbon atoms, and a lithium alkoxide having from 3 to 6 carbon atoms in an inert liquid hydrocarbon, said method comprising mixing a secondary amine having said R' and R" and an alcohol having 3 to 6 carbon atoms with a lithium metal member selected from the group consisting of lithium granulate and lithium powder in an inert liquid hydrocarbon and reacting said secondary amine said alcohol and said lithium metal member with addition of an electron acceptor compound to form the stable non-pyrophoric solution containing said lithium diorganoamide and said lithium alkoxide.

2. The method as defined in claim 1, wherein said R' and R" are each independently selected from the group consisting of an ethyl group, an isopropyl group and a cyclohexyl group.

3. The method as defined in claim 1, wherein said alcohol consists of a tertiary alcohol.

4. The method as defined in claim 1, wherein said electron acceptor compound is selected from the group consisting of styrene and isobutene.

5. The method as defined in claim 1, wherein the inert liquid hydrocarbon is a member selected from the group consisting of aliphatic hydrocarbons having 5 to 10 carbon atoms, cycloaliphatic hydrocarbons having 5 to 10 carbon atoms, aromatic hydrocarbons having 5 to 10 carbon atoms, alkylaromatic hydrocarbons having 5 to 10 carbon atoms and mixtures thereof.

6. The method as defined in claim 1, wherein said stable non-pyrophoric solution contains 0.1 to 2 moles/kg of said lithium diorganoamide.

7. The method as defined in claim 1, wherein said stable non-pyrophoric solution contains said lithium diorganoamide and said lithium alkoxide in a molar ratio of 100:2 to 100:10.

* * * * *